United States Patent

Jorgensen et al.

Patent Number: 5,166,155
Date of Patent: Nov. 24, 1992

[54] QUINOXALINE-2,3-DIONE COMPOUNDS AND THEIR PREPARATION AND USE

[75] Inventors: Anker S. Jorgensen, Copenhagen; Carsten E. Stidsen, Bagsvaerd; Peter Faarup, Vaerlose; Frederik S. Gronvald, Vedbaek, all of Denmark

[73] Assignee: Novo Nordisk A/S, Bagsvaerd, Denmark

[21] Appl. No.: 667,855

[22] Filed: Mar. 12, 1991

[30] Foreign Application Priority Data

Mar. 16, 1990 [DK] Denmark .................... 0697/90

[51] Int. Cl.$^5$ .................. A61K 31/495; C07D 241/52; C07D 241/44
[52] U.S. Cl. .................... 514/249; 544/354
[58] Field of Search .................. 544/354; 514/249

[56] References Cited

U.S. PATENT DOCUMENTS

| 4,948,794 | 8/1990 | Honore et al. ............ 514/250 |
| 5,026,704 | 6/1991 | Honore et al. ............ 514/250 |

FOREIGN PATENT DOCUMENTS 315959  5/1989  European Pat. Off. .

Primary Examiner—Mukund J. Shah
Assistant Examiner—F. Bernhardt
Attorney, Agent, or Firm—Steve T. Zelson; Elias J. Lambiris

[57] ABSTRACT

1-carboxyalkylquinoxaline-2,3(1H,4H)-dione compounds or tautomeric forms thereof of the formula

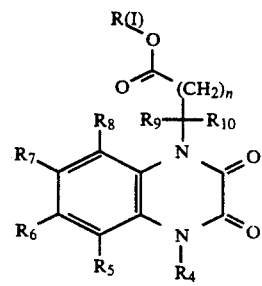

wherein R represents hydrogen, $C_{1-6}$-alkyl, including branched chains, or aralkyl and n represents the number from 0 to 5;

$R^4$ represents hydrogen or hydroxy;

$R^5$, $R^6$, $R^7$ and $R^8$ independently represent hydrogen, nitro, halogen, alkoxy, aryloxy, aralkoxy, $C_{1-6}$-alkyl including branched chains, or aryl;

$R^9$ represents hydrogen, lower alkyl, or aryl;

$R^{10}$ represents hydrogen, or alkyl.

The compounds are useful in the treatment of neurological and psychiatric diseases.

6 Claims, No Drawings

QUINOXALINE-2,3-DIONE COMPOUNDS AND THEIR PREPARATION AND USE

The present invention relates to therapeutically active 1-carboxyalkylquinoxaline-2,3(1H,4H)-dione compounds or tautomeric forms thereof, a method of preparing the same, pharmaceutical compositions comprising the compounds, and a method of treating therewith.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 53, 321 (1985)).

It has been suggested that accumulation of extracellular excitatory and neurotoxic amino acids, followed by hyperstimulation of neurons, may explain the neuronal degenerations seen in neurologicial diseases as Huntingtons chorea, Parkinsonism, epilepsia, senile dementia, and deficiencies of mental and motoric performance seen after conditions of brain ischemia, anoxia and hypoglycemia (E. G. McGeer et al., Nature, 263, 517 (1976) and R. Simon et al., Science, 226, 850 (1984)).

Excitatory amino acids exert their actions via specific receptors located postsynaptically or presynaptically. Such receptors are at present conveniently subdivided into three groups based on electrophysiological and neurochemical evidence: 1 the quisqualate receptors, 2 the kainate receptors, and 3 the NMDA (N-methyl-D-aspartate) receptors. L-glutamic acid and aspartic acid probably activate all the above types of excitatory amino acid receptors and possibly other types as well.

It was recently found that glycine was able to increase NMDA receptor agonist induced responses in cultured neurons (J. W. Johnson et al., Nature 325, 529 (1987)). In contrast to glycine activated chloride conductance in spinal cord neurons, this response was insensitive to strychnine (D. W. Bonhaus et al., European J. Pharmacol. 142, 489 (1987)).

Glycine is believed to potentiate NMDA action through a high affinity binding (H. Kishimoto et al., J. Neurochem. 37, 1015 (1981)) to an allosteric modulatory site located at the NMDA receptor/ionophor complex (T. Honoré et al., European J. Pharmacol. 172, 239 (1989)). D-serine and D-alanine exert a strong agonist activity on this site (J. B. Monahan et al., J. Neurochem. 53, 370 (1989)), whereas 1-amino-cyclopropanecarboxylate (P. Skolnick et al., Life Sci. 45, 1647 (1989), V. Nadler et al., European J. Pharmacol. 157, 115 (1988), R. Trullas et al., Pharmacol. Biochem. Behav., 34, 313 (1989)) and D-cycloserine (W. F. Hood et al., Neurosci. Lett. 98, 91 (1989)) act as partial agonists.

1-amino-cyclobutanecarboxylate (W. F. Hood et al., European J. Pharmacol. 161, 281 (1989)), 1-amino-cyclopentanecarboxylate (L. D. Snell et al., European J. Pharmacol. 151, 165 (1988)), 3-amino-1-hydroxy-2-pyrrolidone (HA-966) (E. J. Fletcher et al., European J. Pharmacol. 151, 161 (1988)), 5-chloro-indole-2-carboxylate (J. E. Huettner, Science 243, 1611 (1989)) and 6-cyano-7-nitroquinoxaline-2,3-dione (CNQX) (R. A. J. Lester et al., Mol. Pharmacol. 35, 565 (1989)) are all weak antagonists, whereas 7-chlorokynurenate (R. Sircar et al., Brain Res. 504, 325 (1989)) and 6,7-dichloro-3-hydroxy-quinoxalin-2-carboxylate (M. Kessler et al., Brain Res. 489, 377 (1989)) are quite strong, but nonselective antagonists of glycine at the glycine site.

Additionally, certain compounds closely related to the present invention claimed as non-NMDA receptor antagonists are disclosed in European Patent Publication No. 315959.

We have now discovered a series of 1-carboxyalkyl-quinoxaline-2,3-dione derivatives acting as potent and selective glycine antagonists at the NMDA receptor-associated glycine site.

The present invention accordingly provides compounds of the formula (I) or tautomeric forms thereof:

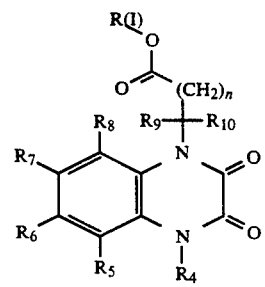

wherein

R represents hydrogen, $C_{1-6}$-alkyl, including branched chains, or aralkyl and n is an integer from 0 to 5;

$R^4$ represents hydrogen or hydroxy;

$R^5$, $R^6$, $R^7$ and $R^8$ independently represent hydrogen, nitro, halogen, alkoxy, aryloxy, aralkoxy, $C_{1-6}$-alkyl including branched chains, or aryl;

$R^9$ represents hydrogen, lower alkyl, or aryl;

$R^{10}$ represents hydrogen, or alkyl, and pharmaceutically acceptable salts thereof.

The invention also relates to a method of preparing the above mentioned compounds. This method comprises:

a) alkylating a compound of the formula (II) (methods for preparation of (II) are cited by G. W. H. Cheeseman and R. F. Cookson. In: The Chemistry of Heterocyclic Compounds (A. Weissberger and E. C. Taylor, eds.). John Wiley & Sons, New York, Vol. 35, p. 78-111 (1979))

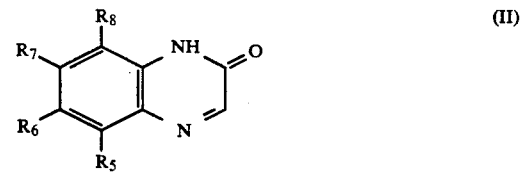

wherein $R^5-R^8$ have the meanings set forth above, with a compound of formula (III)

wherein R, n, $R^9$ and $R^{10}$ are previously defined, provided that R is not hydrogen, and X represents a leaving group, preferably bromine or iodine, to form a compound of formula (IV)

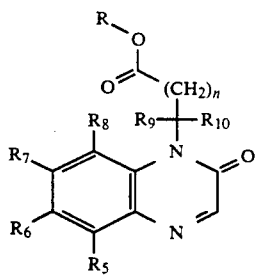

(IV)

wherein R, n $R^5$, $R^6$, $R^7$, $R^8$, $R^9$ and $R^{10}$ have the meanings set forth above, provided that R is not hydrogen.

Oxidation of compound (IV) with aqueous hydrogen peroxide in acetic acid to form a compound of formula (V) (for similar type of reaction see; for example, G. H. W. Cheeseman J. Chem. Soc., 1246 (1961))

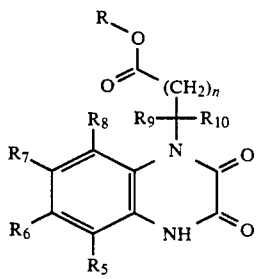

(V)

wherein R, n, $R^5$, $R^6$, $R^7$, $R^8$, $R^9$ and $R^{10}$ have the meanings set forth above, provided that R is not hydrogen.

Hydrolysis of compound (V), or reacting a compound of formula (IV) with aqueous $H_2O_2$/naOH mixture and precipitation with a mineral acid, preferably hydrochloric acid, to form a compound of formula I wherein R and $R^4$ are hydrogen and n, $R^5$, $R^6$, $R^7$, $R^8$, $R^9$ and $R^{10}$ are as previously defined.

b) alkylating a compound of formula (VI) (methods for preparation of (VI), see for example U.S. Pat. No. 3,999,378)

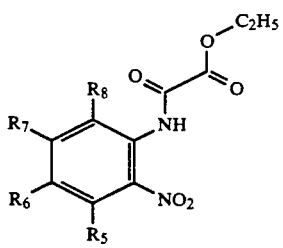

(VI)

wherein R, n, $R^5$, $R^6$, $R^7$, $R^8$, $R^9$ and $R^{10}$ have the meanings set forth above, provided that $R^5$, $R^6$, $R^7$ and $R^8$ is not $NO_2$, with a compound of formula (III), in a suitable solvent, e.g. alcohol or DMF and sodium ethoxide or sodium hydride as base, to form a compound of formula (VII)

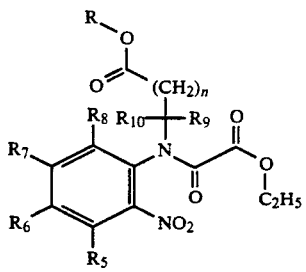

(VII)

wherein
R is preferably tert-butyl
and n and $R^5$, $R^6$, $R^7$, $R^8$, $R^9$, $R^{10}$ have the meanings defined for formula (I), provided that $R^5$, $R^6$, $R^7$ and $R^8$ is not $NO_2$.

Reducing a compound of formula (VII) to form a compound of the formula (VIII)

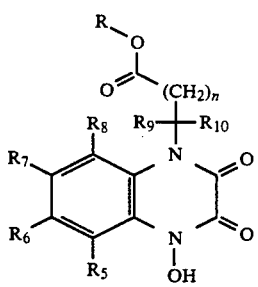

(VIII)

wherein R is preferably tert-butyl and n and $R^5$, $R^6$, $R^7$, $R^8$, $R^9$ and $R^{10}$ have the meanings defined for formula (I), provided that $R^5$, $R^6$, $R^7$ and $R^8$ is not $NO_2$.

Reacting a compound of formula (VIII) to form a compound of formula (I) wherein R represents hydrogen.

c) halogenating or nitrating a compound of formula (IX) by general known methods, (see for example, Jerry March: Advanced Organic Chemistry 3rd ed., McGraw-Hill, New York, 1985, p. 468–70, 476–79)

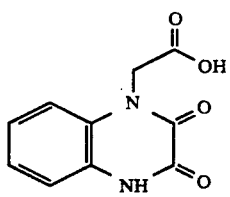

(IX)

to form a compound of formula (I) wherein n=0, and wherein $R^4$, $R^9$ and $R^{10}$ are hydrogen and wherein $R^5$, $R^6$, $R^7$ and $R^8$ are independently hydrogen and halogen or independently hydrogen and $NO_2$.

The affinity of a substance for one or more of the different types of excitatory amino acid receptors may be studied in simple radioligand binding experiments. In essense, the method involves incubation of a particular selected radiolabelled ligand and the particular specific substance to be investigated with brain homogenates which contain the receptor. Measurement of receptor occupancy is made by determination of the radioactivity bound to the homogenate and subtraction of nonspecific binding.

The influence of glutamic acid analogues on secondary effects of glutamate receptor interactions, such as on c-GMP formation and on channel opening, may be studied in vitro by using brain slices or homogenates. Such experiments will provide information as to the efficacies (agonist/antagonist) of the test substances.

It has now been found that the heterocyclic compounds of the invention have affinity for the glycine site of the NMDA receptor complex and are antagonists in connection with this type of receptors, which make them useful in the treatment of any of the numerous diseases caused by hyperactivity of excitatory amino acids, such as epilepsy, ischemia, anxiety states and convulsions.

The glycine site binding activity of these compounds of the present invention can be illustrated by determining their capability for displacing radioactively labelled glycine from the glycine site.

The displacement activity of the compounds may be shown by determining the IC$_{50}$ value which represents the concentration (μM) which causes a displacement of 50% of the specific binding of [$^3$H]-glycine.

The glycine antagonistic properties of the compounds is demonstrated by their capability to antagonize glycine enhanced binding of the non-competitive NMDA antagonist [$^3$H]-MK-801 to brain homogenates. The glycine antagonism is measured by determining the K$_i$ value which represents the dissociation constant (μM) of the receptor-antagonist complex.

The NMDA antagonistic properties of the compounds is illustrated by determining their capability to antagonize NMDA stimulated [$^3$H]-GABA release from cultured mouse cortex neurons. The NMDA antagonistic activity of the compounds may be shown by determining the IC$_{50}$ value, which represents the concentration (μM) which inhibits 50% of NMDA induced [$^3$H]-GABA release.

[$^3$H]-glycine binding (Test 1)

1 ml of thawed rat cerebral cortical membrane homogenate in HEPES-Tris (5 mM) and MgCl$_2$ (1 mM) pH 7.1 were incubated at 0° C. for 10 min. with 25 μl [$^3$H]-glycine (10 nM final concentration) and the test compound and buffer. Non-specific binding was determined by incubating with D-serine (1 mM final concentration). The binding reaction was terminated by centrifugation at 15,000×g at 4° C. followed by washing of the pellet with three times 3 ml of ice-cold buffer. Bound radioactivity was measured by scintillation counting. IC$_{50}$ was determined by Hill analysis of at least four concentrations of test compound.

Antagonism of Glycine Enhanced [$^3$H]-MK-801 Binding (Test 2)

1 ml of thawed and extensively washed rat cerebral membrane homogenate in HEPES-NaOH (20 mM) pH 7.40 were incubated at 23° C. for 60 min. with 25 μl [$^3$H]-MK-801 (1 nM final concentration), 25 μl glutamate (300 nM final concentration), test compound in concentrations corresponding to 0, 0.5, 2 and 5 times the IC$_{50}$ value from the [$^3$H]-glycine binding assay (test 1) for each concentration of glycine (10; 100; 1,000; 10,000 and 100,000 nM final concentration). The binding reaction was terminated by adding 5 ml of ice-cold buffer followed by rapid filtration through Whatman GF/C glass fiber filters and 5 ml wash with ice-cold buffer. Bound radioactivity was measured by scintillation counting. K$_i$ values were determined by Schild analysis of the data using log(dosis ration − 1) = log[Inhibitor] − log(K$_i$).

Inhibition of NMDA Stimulated [$^3$H)-GABA Release From Cultured Mouse Cerebral Cortex Interneurons (Test 3)

Release experiments are performed using the model described by Drejer et al. (Life Sci. 38, 2077 (1986)). To cerebral cortex interneurons cultured in petri dishes (30 mm) are added 100 μg/ml 3-vinyl-GABA one hour before the experiment in order to inhibit degradation of GABA in the neurons. 30 min. before the experiment 5 μCi [$^3$H]-GABA is added to each culture and after this preloading period the cells are washed twice with HEPES buffered saline (HBS) containing 10 mM HEPES, 135 mM NaCl, 5 mM KCl, 0.6 mM MgSO$_4$, 1.0 mM CaCl$_2$ and 6 mM D-glucose; pH 7 and placed in a superfusion system. This system consists of a peristaltic pump continuously delivering thermostated 37° C. superfusion medium from a reservoir to the top of a slightly tilted petri dish. The cell monolayer at the bottom of the dish is covered with a piece of nylon mesh to facilitate dispersion of medium over the cell layer. The medium is continuously collected from the lower part of the dish and delivered to a fraction collector. Initially, the cells are superfused with HBS for 15 min. (flow rate 2 ml/min.). Then cells are stimulated for 30 sec. every 4 min. by changing the superfusion medium from HBS to a corresponding medium containing NMDA and antagonist according to the following scheme:

Stimulation no. 1:3 μg/ml NMDA

Stimulation no. 2:3 μg/ml NMDA+0.3 μg/ml antagonist

Stimulation no. 3:3 μg/ml NMDA+3.0 μg/ml antagonist

The release of [$^3$H]-GABA in the presence of NMDA is corrected for the mean basal release before and after stimulation. The stimulated release in the presence of antagonist is expressed relative to the stimulated release by NMDA alone and the IC$_{50}$ value is calculated.

Test results obtained by testing some compounds employed in the present invention will appear from the following table 1.

TABLE 1

| Compound of Example | Test 1 IC$_{50}$ μM | Test 2 K$_i$ μM | Test 3 IC$_{50}$ μM |
|---|---|---|---|
| 1 | 0.350 | 0.162 | 0.163 |
| 3 | 0.544 | 0.127 | 0.505 |
| 4 | 0.500 | 0.118 | 0.328 |
| 5 | 0.554 | 0.212 | 0.509 |
| 6 | 0.520 | 3.40 | 0.394 |
| 7 | 2.000 | ND | ND |
| 8 | 2.200 | 0.770 | 1.882 |
| 9 | 5.000 | 1.90 | 2.86 |
| 10 | 8.000 | ND | 2.62 |
| 11 | 3.000 | 0.900 | ND |
| 12 | 0.849 | 0.390 | 0.127 |
| 13 | 8.000 | ND | >3.75 |
| 15 | 0.587 | 0.049 | 2.64 |
| 16 | 0.409 | 0.100 | ND |
| 19 | 7.000 | ND | ND |

TABLE 1-continued

| Compound of Example | Test 1 IC$_{50}$ μM | Test 2 K$_i$ μM | Test 3 IC$_{50}$ μM |
|---|---|---|---|
| 22 | 0.852 | ND | ND |

ND: Not determined

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) to two hundred (200) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols', polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| | |
|---|---|
| Active compound | 2.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of effect as glycine antagonists, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic and anxiolytic activities along with a low toxicity, together presenting a most favorable therapeutic index. The compounds of the invention may accordingly be administered to a subject, e.g., a living mammal body, including a human, in need of the same for the treatment, alleviation, amelioration, or elimination of an indication, associated with the central nervous system and the socalled NMDA receptors, which requires such psychopharmaceutical treatment, e.g., especially convulsion, anxiety epilepsy and ischemia, if desired in the form of a pharmaceuticallyacceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their NMDA receptor affinity. Suitable dosage ranges are 1-200 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which may not be construed as limiting:

EXAMPLE 1

1-Carboxymethyl-6,7-dichloroquinoxaline-2,3(1H,4H)-dione

Under a nitrogen atmosphere Na (0.25 g, 11 mmol) was dissolved in 100 ml of abs. ethanol and 6,7-dichloroquinoxalin-2(1H)-one (2.15 g, 10 mmol) (Liebigs Ann. Chem., (1982), 754) was added. The mixture was refluxed for 30 min., cooled to room temperature, and ethyl iodoacetate (1.43 ml, 12 mmol) was added. The clear reaction mixture was refluxed for 2 h during which time a precipitate was formed. This was filtered off, washed with abs. ethanol and dried to afford 2.56 g (85%) of 6,7-dichloro-1-ethoxycarbonylmethylquinoxalin-2(1H)-one. $^1$H-NMR (DMSO-d$_6$):δ1.23 (t, 3H), 4.20 (q, 2H), 5.08 (s, 2H), 8.05 (s, 1H), 8.17 (s, 1H), 8.38 (s, 1H).

The above ester (1.5 g, 5 mmol) was suspended in 70 ml of 2.5% NaOH and 30% $H_2O_2$ (1.95 ml) was added. The mixture was warmed at 70°–80° C. for 5 h, cooled and acidified (pH=1) with concentrated hydrochloric acid. The precipitate was filtered off and recrystallized from DMF-water to afford 1.17 g (81%) of the title compound. M.p. 317°–19° C. $^1$H-NMR (DMSO-$d_6$):δ4.95 (s, 2H), 7.36 (s, 1H), 7.72 (s, 1H), 12.13 (s, 1H), 13.32 (br.s, 1H).

Analysis: Calculated for $C_{10}H_6Cl_2N_2O.H_2O$: C, 39.11; H, 2.63; Cl, 23.09; N, 9.12%. Found: C, 39.11; H, 2.69; Cl, 23.21; N, 9.02%.

EXAMPLE 2

6-Bromo-1-ethoxycarbonylmethylquinoxaline-2,3(1H,4H)-dione

Under a nitrogen atmosphere 6-bromoquinoxalin-2(1H)-one (2.03 g, 9 mmol) (J.Med.Chem., 24, (1981), 93) was dissolved in 22 ml of dry DMF and sodium hydride (0.44 g, 10.8 mmol (60% mineral oil dispersion)) was added. After stirring for 2 h, ethyl bromoacetate (1.25 ml, 11.3 mmol) was added and the mixture was stirred for 3.5 h. The reaction mixture was poured onto crushed ice and acidified (pH=4.5) by addition of dilute hydrochloric acid. The precipitate was filtered off, washed with water and air dried. The crude product (containing a minor fraction of O-alkylated product) was triturated with ether (100 ml), the precipitate filtered off, washed with ether and dried to afford 1.95 g (80%) of pure 6-bromo-1-ethoxycarbonylmethyl-quinoxalin-2(1H)-one. $^1$H-NMR (DMSO-$d_6$):δ1.22 (t, 3H), 4.17 (q, 2H), 5.08 (s, 2H), 7.56 (d, 1H), 7.83 (dd, 1H), 8.09 (dd, 1H), 8.37 (s, 1H).

The above ester (1.25 g; 4 mmol) was reacted with 30% $H_2O_2$ (6 ml) in glacial acetic acid (16 ml) at 55° C. for 2 h. The mixture was cooled, the precipitate filtered off and recrystallized from dilute acetic acid to afford 1.0 g (77%) of the title compound. M.p. 282°–83° C. $^1$H-NMR (DMSO-$d_6$):δ1.22 (t, 3H), 4.17 (q, 2H), 4.92 (s, 1H), 7.33 (m, 3H), 12.24 (br.s, 1H).

EXAMPLE 3

6-Bromo-1-carboxymethylquinoxaline-2,3(1H,4H)-dione

The ester of example 2 (0.33 g, 1 mmol) was reacted with 4% NaOH (9 ml) for 3 h at room temperature. The mixture was cooled in an ice bath and the pH was adjusted to 1 with 4M hydrochloric acid. The precipitate was filtered off, washed with water and recrystallized from acetic acid to afford 0.21 g (70%) of the title compound. M.p. >320° C. $^1$H-NMR (DMSO-$d_6$): 4.86 (s, 1H), 7.29 (m, 3H), 12.24 (s, 1H), 13.28 (br.s, 1H).

Analysis: Calculated for $C_{10}H_7BrN_2O_4.H_2O$: C, 40.16; H, 2.36; Br, 26.72; N, 9.36%. Found: C, 40.06; H, 2.37; Br, 26.93; N, 9.22%.

EXAMPLE 4

1-Carboxymethyl-6,7-difluoroquinoxaline-2,3(1H,4H)-dione 4,5-difluoro-2-nitroaniline (2.17 g, 12.5 mmol) was dissolved in 55 ml of ethanol and 250 mg of 10% palladium on carbon was added. The mixture was hydrogenated until the theoretical amount of hydrogen had been absorbed, using a low pressure hydrogenation apparatus. The catalyst was filtered off and the filtrate, containing 4,5-difluoro-o-phenylenediamine, was kept under a nitrogen atmosphere at 0° C. followed by addition of a solution of glyoxylic acid hydrate (1.28 g, 13.7 mmol) in water (3 ml). When the addition was complete the reaction temperature was allowed to reach room temperature during 2 h and 30 ml of water was added. The precipitate was filtered off and dissolved in 60 ml of 5% NaOH solution at 50° C. followed by addition of activated carbon. The mixture was filtered and the filtrate was acidified (pH=1) by addition of concentrated hydrochloric acid. The pinky precipitate was filtered off, washed with water and dried to afford 1.25 g (55%) of 6,7-difluoroquinoxalin-2(1H)-one melting at 284°–85° C. $^1$H-NMR (DMSO-$d_6$): 7.27 (m, 1H), 7.95 (m, 1H), 8.20 (s, 1H), 12.55 (s,1H).

6,7-Difluoroquinoxalin-2(1H)-one (1.1 g, 6 mmol) was reacted following the procedure of example 1 to afford the title compound melting with destruction at 315°–16° C. $^1$H-NMR (DMSO-$d_6$):δ4.86 (s, 2H), 7.16 (m, 1H), 7.65 (m, 1H), 12.27 (s, 1H), 13.30 (br.s, 1H).

Analysis: Calculated for $C_{10}H_7N_2F_2O_4.H_2O$: C, 43.81; H, 2.94; N, 10.22%. Found: C, 43.85; H, 2.94; N, 10.22%.

EXAMPLE 5

1-Carboxymethyl-6,7-dimethylquinoxaline-2,3(1H,4H)-dione

The title compound was prepared employing the procedure described in example 1 starting from 6,7-dimethylquinoxalin-2(1H)-one (Liebigs Ann.Chem., (1982), 754). M.p. 308°–10° C. (dec.). $^1$H-NMR (DMSO-$d_6$):δ2.19 (s, 3H), 2.22 (s, 3H), 4.84 (s, 2H), 6.96 (s, 1H), 7.11 (s, 1H), 12.05 (s, 1H), 13.18 (br.s., 1H).

Analysis: Calculated for $C_{12}H_{12}N_2O_4 \cdot 1\frac{1}{2}H_2O$: C, 52.36; H, 5.49; N, 10.18%. Found: C, 52.45; H, 5.28; N, 10.14%.

EXAMPLE 6

1-Carboxymethyl-6-chloroquinoxaline-2,3(1H,4H)-dione

In accordance with the procedure described in example 1 the title compound was prepared starting from 6-chloroquinoxalin-2(1H)-one (Heterocycles, 23, (1985), 143). M.p. 318°–19° C. $^1$H-NMR (DMSO-$d_6$):δ4.88 (s, 2H), 7.30–7.40 (m, 3H), 12.25 (s, 1H), 13.32 (br.s, 1H).

Analysis: Calculated for $C_{10}H_7N_2ClO_4$: C, 47.17; H, 2.77; N, 11.00; Cl, 13.92%. Found: C, 47.12; H, 2.79; N, 10.96; Cl, 13.89%.

EXAMPLE 7

1-Carboxymethyl-6-nitroquinoxaline-2,3(1H,4H)-dione 6-nitroquinoxalin-2(1H)-one (J.Chem.Soc. (1961), 1246) was reacted in accordance with the procedure described in example 2 yielding 1-ethoxycarbonylmethyl-6-nitroquinoxaline-2,3(1H,4H)- dione, which after recrystallization from dilute acetic acid had M.p. 252°–54°. $^1$H-NMR (DMSO-$d_6$):δ1.23 (t, 3H), 4.17 (q, 2H), 5.02 (s, 2H), 7.56 (d, 1H), 8.00 (dd, 1H), 8.01 (d, 1H), 12.48 (s, 1H).

The above ester (0.29 g, 1 mmol) was suspended in 1.25 ml of 2M NaOH and 10 ml of water and stirred for 3 h at 0° C. The clear solution was maintained at 0° C. and the pH was adjusted to 1 by addition of 4 M HCl. The precipitate was filtered off, washed with water and recrystallized from dilute acetic acid to afford 0.13 g (50%) of the title compound. M.p.>320° C. $^1$H-NMR (DMSO-d$_6$):δ4.96 (s, 2H), 7.56 (d, 1H), 8.02 (dd, 1H), 8.06 (d,1H), 12.52 (s, 1H), 13.42 (br.s, 1H).

EXAMPLE 8

1-((1-Carboxy)pentyl)-quinoxaline-2,3(1H,4H)-dione

Quinoxalin-2(1H)-one (2.00' g, 13.7 mmol) was suspended in 40 ml of dry DMF under nitrogen. Sodium hydride (0.66 g, 16.4 mmol (60% mineral oil dispersion)) was added and the mixture was stirred for 1 h. Ethyl 2-bromohexanoate (3.87 g, 16.4 mmol) was added, and the mixture was stirred at room temperature for 20 h and at 70° C. for 5.5 h, then poured onto crushed ice and acidified by dilute hydrochloric acid. The precipitated oil was extracted with ethyl acetate and purified by column chromatography on silica gel (eluent 15% THF in heptane) to afford 1.89 g of the O-alkylated compound and 0.46 g of the desired N-alkylated product, 1-((1-ethoxycarbonyl)pentyl)quinoxaline-2(1H)-one. $^1$H-NMR (DMSO-d$_6$):δ0.78 (t, 3H), 1.09 (t, 3H), 1.15–1.36 (m, 4H), 2.04–2.32 (m, 2H), 4.02–4.18 (m, 2H), 5.6–5.9 (m, 1H), 7.42 (t, 1H), 7.67 (t, 1H), 7.65–7.82 (br.s, 1H), 7.90 (d, 1H), 8.28 (s, 1H).

The above ester (0.40 g, 1.39 mmol) was reacted with 30% H$_2$O$_2$ (2.2 ml) in glacial acetic acid (5.8 ml) at 55° C. for 20 h. The mixture was poured onto crushed ice and extracted with ethyl acetate (2×75 ml). The combined organic extract was dried (Na$_2$SO$_4$) and evaporated in vacuo to an oil, which was reacted with 0.5M NaOH (7 ml) for 4 h at room temperature. The solution was acidified with 1M HCl to pH 2.0 and the precipitate was filtered off, washed with water and then with ether to afford 166 mg of the title compound. M.p. 253°–55° C. $^1$H-NMR (DMSO-d$_6$):δ0.80 (t, 3H), 1.04–1.36 (m, 4H), 1.95–2.30 (m, 2H), 5.1–5.9 (m, 1H), 7.2 (m, 3H), 7.2–7.8 (m, 1H), 12.2 (s, 1H), 12.9 (br.s, 1H).

Analysis: calculated for C$_{14}$H$_{16}$N$_2$O$_4$:C, 60.86; H, 5.84; N, 10.14%. Found: C, 60.46; H, 5.86; N, 10.56%.

The compounds mentioned in examples 9, 10 and 11 were prepared using essentially the same procedure outlines in example 8 above, starting from quinoxalin-2(1H)-one. cl EXAMPLE 9

1-((1-Carboxy)butyl)quinoxaline-2,3(1H,4H)-dione (The alkylation reaction was performed with ethyl 2-bromopentanoate as alkylating agent and diglyme as solvent by heating to reflux for 2 h). M.p. 272°–75° C. $^1$H-NMR (DMSO-d$_6$):δ0.83 (t, 3H), 1.05–1.38 (m, 2H), 1.95–2.20 (m, 2H), 5.1–5.9 (br.m, 1H) (by heating the probe to 100° C. the band appears as a triplet at 5.5), 7.1–7.25 (m, 3H), 7.2–7.9 (br.m, 1H) (by heating the probe to 100° C. the band appears as a sharp multiplet at 7.25), 12.2 (s, 1H), 12.85 (br.s, 1H).

EXAMPLE 10

1-(1-Carboxy-1-phenylmethyl)quinoxaline-2,3(1H,4H)-dione (The alkylation reaction was performed with ethyl 2-bromo-2-phenylacetate as alkylating agent, ethanol as solvent, and sodium ethoxide as base by heating to reflux for 72 h). M.p. 242°–44° C. $^1$H-NMR (DMSO-d$_6$):δ6.04 (s, 1H), 7.0–7.55 (m, 9H), 12.23 (s, 1H), 13.1 (br.s, 1H).

EXAMPLE 11

1-((1-Carboxy)ethyl)quinoxaline-2,3(1H,4H)-dione (The alkylation reaction was performed with ethyl 2-bromopropionate as alkylating agent, DMSO as solvent, potassium carbonate (2 equivalents) as base and potassium iodide (0.1 equivalent) as catalyst by heating to 85° C. for 4 h). M.p. 301°–303° C. (decomp.). $^1$H-NMR (DMSO-d$_6$):δ1.47 (d,3H), 5.47 (broad signal, 1H), 7.1–7.5 (m, 4H), 12.13 (s, 1H), 12.8 (br.s, 1H).

EXAMPLE 12

1-Carboxymethyl-6,7-dibromoquinoxaline-2,3(1H,4H)-dione

1-Carboxymethylquinoxaline-2,3(1H,4H)-dione (0.50 g, 2.27 mmol) (Indian J. Chem. 20B, (1981), 822) and Ag$_2$SO$_4$ (0.744 g, 2.384 mmol) was suspended in 98% H$_2$SO$_4$ (2.3 ml). Bromine (0.244 ml, 4.77 mmol) was added and the mixture was stirred at room temperature for 24 h, then tetrachloromethane (2.3 ml) was added and the reaction mixture was stirred at 50° C. for 2 h, filtered and the filtrate was poured onto crushed ice (20 ml). The precipitate was filtered off, washed with water and dried to afford 0.57 g of crude product. Purification was performed by dissolving the crude substance in 10 ml of 1M sodium hydroxide (pH=12) followed by precipitation with 1M hydrochloric acid (pH=2) M.p.>300 (decomp.). $^1$H-NMR (DMSO-d$_6$):δ4.82 (s, 2H), 7.47 (s, 1H), 7.71 (s, 1H), 12.29 (s, 2H).

EXAMPLE 13

1-Carboxymethyl-4-hydroxy-6-methoxyquinoxalin-2,3(1H,4H)-dione

4-Methoxy-2-nitroaniline (16.8 g, 0.1 mol) was dissolved in 300 ml of pyridine under nitrogen and cooled to −10° C., and dimethylaminopyridine (1.22 g, 0.01 mol) was added. The mixture was stirred and a solution of ethyl oxalylchloride (21.4 g, 0.157 mol) in 50 ml of tetrahydrofuran was added over a period of 15 min. After the addition was complete the reaction mixture was kept at −20° C. overnight, and poured onto 1 l of ice-water. The separated solid was collected and dried to afford 25.0 g (93%) of ethyl N-(4-methoxy-2-nitrophenyl)oxamate. M.p. 156°–57° C. $^1$H-NMR (CDCl$_3$):δ1.41 (t, 3H), 3.85 (s, 3H), 4.42 (q, 2H), 7.20 (dd, 2H), 7.70 (d, 1H), 8.70 (d, 1H), 11.6 (s, 1H).

The above prepared oxamate (5.35 g, 0.02 mol) was dissolved in 50 ml of DMF under N$_2$ and NaH (0.96 g, 0.024 mol (60% mineral oil dispersion)) was added under stirring at room temperature. After 1 h tert-butyl bromoacetate (4.78 g, 0.024 mol) was added and stirring was continued at room temperature for 3 h. The reaction mixture was poured into water and was extracted with ethyl acetate. The organic phase was dried and evaporated to afford 4.1 g (55%) of ethyl N-(tert-butoxycarbonylmethyl)-N-(4-methoxy-2- nitrophenyl)oxamate. $^1$H-NMR (DMSO- d$_6$):δ0.90 (t, 3H), 1.42 (s, 9H), 3.89 (s, 3H), 3.95 (q, 2H), 4,35 (dd, 2H), 7.46 (dd, 1H), 7.60 (d, 1H), 7.73 (d, 1H).

1 g of the above prepared compound was dissolved in 150 ml of ethanol and under a nitrogen atmosphere was added 0.25 g Pd/C 10%. The hydrogenation was carried out in a Parr apparatus at 50 psi during 3 h. The catalyst was removed by filtration and the filtrate was evaporated to dryness giving raw 1-tert-butoxycarbonylmethyl-4-hydroxy-6-methoxyquinoxaline-3,4(1H,4H)-dione (0.51 g) (55%). $^1$H-NMR (DMSO-d$_6$):δ1.42 (s, 9H), 3.86 (s, 3H), 4.96 (s, 2H), 6.9 (dd, H), 7.35 (d, H), 7.54 (d, H), 11.8 (br.s, H). M.p. 250° C. (decomp.).

0.5 g of the above prepared compound was treated with HCl in dioxane (16 ml, 2.5M) at room temperature for 24 h. During this period a white solid separated. The solid was collected by filtration, washed with cold methanol and dried to afford 1-carboxymethyl-4-hydroxy-6-methoxy-quinoxaline-3,4-(1H,4H)-dione (0.220 g) (40%). Purity HPLC 98%. $^1$H-NMR (DMSO-$d_6$):δ3.82 (s, 3H), 4.92 (s, 2H), 6.89 (dd, 1H), 7.11 (d, 1H), 7.33 (d, 1H), 12.0 (br.s, 1H) 13.28 (br.s, 1H). M.p.>275° C.

Analysis: Calculated for $C_{11}H_{11}N_2O_6$. 0.25 $H_2O$: C, 48.80; H, 3.90; N, 10.35%. Found: C, 48,91; H, 3.88; N, 10.04%.

EXAMPLE 14

1-((1-Ethoxycarbonyl)hexyl)-6-bromoquinoxaline-2,3(1H,4H)-dione

Under a nitrogen atmosphere sodium (1.40 g, 61 mmol) was dissolved in 400 ml of abs. ethanol and 6-bromoquinoxalin-2(1H)-one (11.93 g, 53 mmol)(J. Med. Chem., 24, (1981), 93) was added. The mixture was stirred until the compound dissolved and ethyl 2-bromoheptanoate, (12.71 ml, 63.6 mmol) was added. The reaction mixture was refluxed for 72 h, cooled to room temperature, then poured onto a mixture of 200 ml crushed ice, 200 ml 1M hydrochloric acid and 500 ml dichloromethane.

The organic phase was separated, washed with 100 ml of 1M hydrochloric acid and 100 ml of water, filtered, dried and evaporated to give an oil, which was purified by column chromatography on silica gel (eluent 3% THF in heptane) to afford 3.61 g of 1-((1-ethoxycarbonyl)hexyl)6-bromoquinoxaline-2(1H)-one. $^1$H-NMR(DMSO-$d_6$):δ0.78(t, 3H), 1.09(t, 3H), 1.11-1.35(m, 6H), 2.0-2.3(m, 2H), 4.02-4.18(m, 2H), 5.54-5.86(m, 1H), 7.5-7.8(br.m, 1H), 7.85(dd, 1H), 8.09(d, 1H), 8.33(s, 1H).

The above ester (3.43 g, 9.0 mmol) was reacted with 30% $H_2O_2$ (14.9 ml) in glacial acetic acid (40 ml) at 55° C. for 20h. The mixture was poured onto crushed ice (250 ml) and extracted with ethyl acetate (2×400 ml). The combined organic extract was washed with half saturated sodium hydrogen carbonate solution and water, dried ($Na_2SO_4$), evaporated to dryness and stripped with ether. The product was triturated with heptane (20 ml) overnight, the precipitate filtered off, washed with heptane and dried to afford 2.86 g of the title compound. M.p. 187°-190° C. $^1$H-NMR(DMSO-$d_6$):δ0.80(m, 3H), 1.1(t, 3H), 1.12-1.4(m, 6H) 1.9-2.25(m, 2H), 4.0-4.17(m, 2H), 5.2-5.7(m, 3H), 12.28(s, 1H).

Analysis: Calculated for $C_{17}H_{21}N_2O_4Br$: C,51.39; H, 5.33; N, 7.05; Br, 20.12% Found: C, 51.49; H, 5.43; N, 7.02; Br, 20.24%.

EXAMPLE 15

1-((1-Carboxy)hexyl)-6-bromoquinoxaline-2,3(1H, 4H)-dione

The ester of example 14 (1.40 g, 3.52 mmol) was suspended in 19.21 ml of 0.5M NaOH and stirred for 20h at room temperature. The reaction mixture was filtered and the pH was adjusted to 2 by addition of 1M HCl. After cooling in an ice bath the precipitate was filtered off and washed with water to afford 1.21. g of the title compound. M.p. 265°-267° C. $^1$H-NMR(DMSO-$d_6$):δ0.79(m, 3H), 1.08-1.37(m, 6H), 1.87-2.25 (m, 2H), 5.1-5.7(m, 1H), 7.25-7.8(m, 3H), 12.25(s, 1H), 12.5-13.2(br.s, 1H).

Analysis: Calculated for $C_{15}H_{17}N_2O_4Br.\frac{1}{2}H_2O$: C, 47.63; H, 4.80; N, 7.41%. Found: C, 47.80; H, 4.65; N, 7.59%.

EXAMPLE 16

1-((1-carboxy)pentyl)-6,7-dichloroquinoxaline-2,3(1H,4H)-dione

Under a nitrogen atmosphere sodium (0.148 g, 6.42 mmol) was dissolved in 50 ml of abs. ethanol and 6,7-dichloroquinoxalin-2(1H)-one (1.20 g, 5.58 mmol) (Liebigs Ann. Chem., (1982), 754) was added. The mixture was stirred until the compound dissolved, and ethyl 2-bromohexanoate (1.30 ml, 7.1 mmol) was added. The reaction mixture was refluxed for 72 h, cooled to room temperature, then poured onto crushed ice and acidified by dilute hydrochloric acid (pH=2). The precipitated compound was extracted with ethyl acetate and purified by column chromatography on silica gel (eluent 15% THF in heptane) to afford 0,21 g of 1-((1-ethoxycarbonyl)pentyl)-6,7-dichloroquinoxalin-2(1H)-one $^1$H-NMR(DMSO-$d_6$):δ 0.78(t, 3H), 1.1(t, 3H), 1.15-1.35(m, 4H), 2.0-2.25(m, 2H), 4.02-4.18(m, 2H), 5.58-5.75(m, 1H), 8.02-8.36(broad, 1H), 8.18(s, 1H), 8.33(s, 1H).

The above ester (0.16 g, 0.448 mmol) was suspended in 3 ml of 5% NaOH and 30% $H_2O_2$ (0.175 ml) was added. The mixture was warmed at 80° C. under stirring for 5 h, cooled and acidified (pH=1) with 5M hydrochloric acid. The precipitate was filtered off, washed with water and dried to afford 90 mg of the title compound. 1H-NMR(DMSO-$d_6$):δ0.81(t, 3H), 1.03-1.33(m, 4H), 1.82-2.23(m, 2H), 5.22-5.5(m, 1H), 7.35(s, 1H), 7.5-8.2(broad, 1H), 12.3(s, 1H), 12.6-13.3(br.s, 1H).

EXAMPLE 17

1-Phenylmethyloxycarbonylmethyl-6,7-dichloroquinoxaline-2,3(1H, 4H)-dione

Under a nitrogen atmosphere 6,7-dichloroquinoxalin-2(1H)-one (10.0 g, 46.5 mmol) (Liebigs Ann. Chem, (1982), 754) was suspended in 135 ml of dry DMF and sodium hydride (2.23 g, 55.8 mmol (60% mineral oil dispersion)) was added. After stirring for 2 h, benzyl bromoacetate (9.18 ml, 58.6 mmol) was added and the mixture was stirred for 3.5 h. The reaction mixture was poured onto 300 g of crushed ice and the precipitate was filtered off, washed with water and dried. The product was triturated with ether (500 ml), the precipitate filtered off, washed with ether and dried to afford 13.3 g of 1-benzyloxycarbonylmethyl-6,7-dichloroquinoxaline-2(1H)-one. $^1$H-NMR (DMSO-$d_6$):δ5.18(s, 2H), 5.23(s, 1H), 8.18(s, 1H), 8.38(s, 1H).

The above ester (12.0 g, 33 mmol) was reacted with 30% $H_2O_2$ (50 ml) in glacial acetic acid (350 ml) at 55° C. for 24 h. The mixture was cooled and 600 ml of icecold water was added. The precipitate was filtered off and recrystallized from DMF-water to afford 7.16 g of the title compound. M.p. 286°-289° C. $^1$H-NMR(DMSO-$d_6$):δ5.08(s, 2H), 5.22(s, 2H), 7.28-7.45(m, 6H), 7.75(s, 1H), 12.35(s, 1H).

Analysis: Calculated for $C_{17}H_{12}N_2O_4Cl_2$: C, 53.84; H, 3.19; N, 7.39; Cl, 18.70%. Found: C, 53.65; H, 3.26; N, 7.44; Cl, 18.52%.

EXAMPLE 18

1-Tert-butoxycarbonylmethyl-6,7-dichloroquinoxaline-2,3(1H,4H)-dione

The title compound was prepared using essentially the same procedure outlined in example 17. The alkylation reaction was performed with tert-butylbromoacetate as alkylating agent, ethanol as solvent and sodium ethoxide as base by heating to reflux for 20 h. M.p.>300° C. $^1$H-NMR(DMSO-d$_6$):δ1.43(s, 9H), 4.88(s, 2H), 7.35(s, 1H), 7.66(s, 1H), 12.32(s, 1H).

EXAMPLE 19

1-Carboxymethyl-7-nitroquinoxaline-2,3(1H,4H)-dione

Under a nitrogen atmosphere 7-nitroquinoxalin-2(1H)-one (3.06 g, 16 mmol) (J Chem. Soc. (1961), 1246) was dissolved in 40 ml of dry DMF and sodium hydride (0.768 g, 19.2 mmol (60% mineral oil dispersion)) was added. After stirring for 1.5 h, ethyl bromoacetate (2.22 ml, 20 mmol) was added and the mixture was stirred for 3 h. The reaction mixture was poured onto crushed ice and acidified (pH=4.5) by addition of dilute hydrochloric acid. The precipitate was filtered off, washed with water and air dried. Purification was performed by column chromatography on silica gel (eluent 1–10% THF in heptane). The faster moving fraction (R$_F$=0.68, THF/heptane (1:1)) was collected and evaporated to afford 0.78 g (17%) of 2-ethoxycarbonylmethyloxy-7-nitroquinoxaline-2(1H)-one. $^1$H-NMR (DMSO-d$_6$): 1.22 (t, 3H), 4.20 (q, 2H), 5.18 (s, 2H), 8.28 (d, 1H), 8.39 (dd, 1H), 8.43 (dd, 1H), 8.97 (s, 1H). The slower moving fraction (R$_F$=0.62, THF/heptane (1:1)) was collected and evaporated to afford 1.54 g (35%) of 1-ethoxycarbonylmethyl-7-nitroquinoxaline-2(1H)-one. $^1$H-NMR (DMSO-d$_6$):δ1.23 (t, 3H), 3.32 (q, 2H), 4.19 (q, 2H), 5.20 (s, 2H), 8.11 (d, 1H), 8.17 (dd, 1H), 8.40 (d, 1H), 8.50 (s, 1H).

The latter compound (1,0 g, 3.6 mmol) was reacted with 30% H$_2$O$_2$ (5,4 ml) in glacial acetic acid (15 ml) at 56° C. for 16 h. The mixture was cooled, the precipitate filtered off, washed with water and dried to afford 0,8 g (76%) of 1-ethoxycarbonylmethyl-7-nitroquinoxaline-2,3(1H,4H)-dione. $^1$H-NMR (DMSO-d$_6$):δ1.24 (t, 3H), 4.20 (q, 2H), 5.10 (s, 2H), 7.36 (d, 1H), 8.12 (dd, 1H), 8.17 (dd, 1H), 12.72 (br. s, 1H).

The above ester (0.4 g, 1.36 mmol) was reacted with 2M NaOH (3.9 ml) for 1 h at room temperature. The mixture was cooled in an ice bath and the pH was adjusted to 1 with 4M hydrochloric acid. The precipitate was filtered off, washed with water and dried to afford 0.34 g (88%) of the title compound. M.p. 305°-306° C. $^1$H-NMR (DMSO-d$_6$):δ5.02 (s, 2H), 7.37 (d, 1H), 8.12 (m, 2H), 12.70 (s, 1H), 13.40 (br. s, 1H).

Analysis: Calculated for C$_{10}$H$_7$N$_3$O$_6$. H$_2$O: C, 42.41; H, 3.20; N, 14.83%. Found: C, 42.71; H, 3.35; N, 14.65%.

Alternatively 1-carboxymethylquinoxaline-2,3(1H, 4H)-dione (Indian J. Chem. 20B, (1981), 822) could be nitrated using excess of 75% HNO$_3$ in a mixture of acetic anhydride and acetic acid at 0° C. to give the title compound.

EXAMPLE 20

1-Carboxymethyl-7-chloro-4-hydroxyquinoxaline-2,3(1H,4H)-dione

A solution of 5-chloro-2-nitroaniline (3.0 g, 17 mmol) and 4-dimethylaminopyridine (0.21 g, 1.7 mmol) in 30 ml of pyridine was stirred at −10° C. and a solution of ethyl oxalyl chloride (3.5 g, 26 mmol) in 10 ml of tetrahydrofuran was added dropwise. After the addition was complete the ice bath was removed and stirring was continued for 7 h. The reaction mixture was poured onto crushed ice, the precipitate was filtered off, washed with water and dried to afford 4.4 g (97%) of ethyl N-(3-chloro-6-nitrophenyl)oxamate. M.p. 103°-4° C. $^1$H-NMR (DMSO-d$_6$):δ1.33 (t, 3H), 4.34 (q, 2H), 7.52 (dd, 1H), 8.19 (d, 1H), 8.24 (d, 1H), 11.46 (br.s, 1H).

Under a nitrogen atmosphere ethyl N-(3-chloro-6-nitrophenyl)oxamate (4.09 g, 15 mmol) was dissolved in 35 ml of dry DMF and sodium hydride (0.67 g, 16.8 mmol) was added portionwise. After the evolution of hydrogen had subsided t-butyl bromoacetate (3.5 g, 18 mmol (60% mineral oil dispersion)) was added and the mixture was stirred overnight at room temperature. The reaction mixture was poured onto ice and extracted with dichloromethane (3×50 ml). The combined organic extracts was washed with water, dried over Na$_2$SO$_4$ and filtered. The solvent was evaporated leaving a slightly yellow oil (4.4 g) having $^1$H-NMR (DMSO-d$_6$):δ0.96 (t, 3H), 1.44 (s, 9H), 4.00 (q, 2H), 4.42 (dd, 2H), 7.78 (d, 1H), 7.84 (dd, 1H), 8.24 (d, 1H) assigned to ethyl (N-(t-butoxycarbonylmethyl)- N-(3-chloro-6-nitrophenyl)oxamate.

A mixture of the latter crude oil (1.93 g, 5 mmol) and 0.19 g of 10% Pd/C in 65 ml of ethanol was hydrogenated at 50 psi for 5h using a Parr apparatus. The catalyst was removed by filtration and the filtrate was evaporated in vacuo to afford 1.1 g (70%) of 1-(t-butoxycarbonylmethyl)-7-chloro-4-hydroxyquinoxaline-2,3(1H,4H)-dione. $^1$H-NMR (CDCl$_3$):δ1.42 (s, 9H), 4.84 (s, 2H), 7.00-7.72 (m, 3H).

The above ester (1.08 g, 3.5 mmol) was dissolved in 8 ml of dioxane and a solution of HCl in dioxane (8 ml, 5M) was added. The mixture was refluxed for 2 h during which time a precipitate was formed. This was filtered off and purified by dissolving in 10% NaOH solution, decolourising with activated carbon and reprecipitation with hydrochloric acid (pH=1) to afford 0.37 g (35%) of the title compound. M.p. 280°-82° C. $^1$H-NMR (DMSO-d$_6$):δ4.95 (s, 2H), 7.37 (dd, 1H), 7.60 (m, 2H), 12.00 (br.s, 1H), 13.55 (br.s, 1H).

Analysis: Calculated for C$_{10}$H$_7$Cl N$_2$O$_5$. 2H$_2$O: C, 39.17; H, 3.61; Cl, 11.56; N, 9.13%. Found: C, 39.29; H, 3.72; Cl, 11.30; N, 9.01%.

EXAMPLE 21

1-Ethoxycarbonylmethyl-6,8-dichloroquinoxaline-2,3(1H,4H)-dione

A mixture of 2,4-dichloro-6-nitroaniline (7.7 g, 37.2 mmol) and SnCl$_2$ (21.6 g, 111.6 mmol) were mechanically stirred under a nitrogen atmosphere. Hydrochloric acid (38.5 ml) was added and the mixture was warmed at 75°-80° C. for 2 h. The mixture was cooled (ice bath) and neutralized (pH=9) with 50% potassium hydroxide solution followed by extraction with ether (3×150 ml). The combined organic extracts was dried over sodium hydroxide pellets and filtered. The solvent was evaporated leaving 6.2 g of intermediary 1,2-diamino-3,5-dichlorobenzene, which was dissolved in 200 ml of methanol and stirred under cooling in an ice bath. Hydrochloric acid (2.90 ml) was added followed by addition of glyoxylic acid monohydrate (3.9 g, 42.4 mmol). The ice bath was removed and stirring was continued for 16 h. The precipitate was filtered off, washed with cold methanol and dried to afford 6.0 g isomeric mixture (6:1, $^1$H-NMR) of 6,8-dichloroquinoxalin-2(1H)-one and 5,7-dichloroquinoxalin-2(1H)-one, respectively. The isomeric mixture was recrystallized from 2-methoxyethanol (100 ml) to afford 3.4 g of 6,8-dichloroquinoxalin-2-(1H)-one. M.p. 228°–229° C. $^1$H-NMR (DMSO-d$_6$):δ7.88 (m, 2H), 8.30 (s, 1H), 12.20 (s, 1H).

Under a nitrogen atmosphere sodium (0.13 g, 5.62 mmol) was dissolved in 25 ml of abs. ethanol and 6,8-dichloroquinoxalin-2(1H)-one (1.10 g, 5.11 mmol) was added. The mixture was refluxed for 20 min., and ethyl iodoacetate (0.729 ml, 6.13 mmol) was added. The reaction mixture was refluxed for 72 h, cooled to room temperature, then poured onto crushed ice and acidified by dilute hydrochloric acid (pH=2). The precipitated compound was extracted with dichloromethane (4×30 ml) and purified by column chromatography on silica gel (eluent 10% THF in heptane) to give 1-ethoxycarbonylmethyl-6,8-dichloroquinoxalin-2(1H)-one. $^1$H-NMR (DMSO-d$_6$):δ1.23 (t, 3H), 4.22 (q, 2H), 5.29 (s, 2H), 7.97 (dd, 2H), 8.45 (s, 1H).

The above ester, (70 mg, 0.23 mmol) was reacted with 30% H$_2$O$_2$ (0.345 ml) in glacial acetic acid (0.92 ml) at 55° C. for 4.5 h. The mixture was cooled in an icebath and H$_2$O (0.40 ml) was added. The precipitate was filtered off, washed with water and dried to give 35 mg (48%) of the title compound. $^1$H-NMR (DMSO-d$_6$):δ1.23 (t, 3H), 4.20 (q, 2H), 5.02 (s, 2H), 7.21 (d, 1H), 7.42 (d, 1H), 12.3 (s, 1H).

EXAMPLE 22

1-Carboxymethyl-6,8-dichloroquinoxaline-2,3(1H, 4H)-dione

The ester of example 21 (34 mg, 0.107 mmol) was reacted with 0.1M NaOH (3.2 ml) in a mixture of THF (2.0 ml) and water (0,5 ml) for 26 h at 45° C. The solvent was removed in vacuo and the remanens was dissolved in water (1.0 ml), cooled in an ice bath and the pH was adjusted to 2.5 with 0.5 M hydrochloric acid. The precipitate was filtered off, washed with water and dried to give 20 mg (65%) of the title compound. $^1$H-NMR (DMSO-d$_6$):δ5.0 (s, 2H), 7.2 (d, 1H), 7.41 (d, 1H), 12.33 (s, 1H), 13.18 (br.s, 1H).

We claim:

1. A compound of formula I

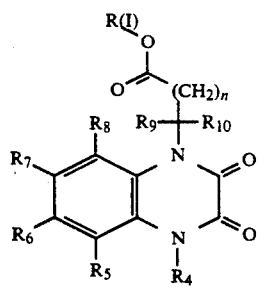

wherein
R is hydrogen, branched or unbranched C$_{1-6}$-alkyl or phenyl lower alkyl;
n is an integer from 0 to 5;
R$^4$ is hydroxy;
R$^5$, R$^6$, R$^7$ and R$^8$ independently are hydrogen, nitor, halogen, methoxy or branched or unbranched C$_{1-6}$-alkyl;
R$^9$ is hydrogen, C$_{1-5}$-alkyl or phenyl; and
R$^{10}$ is hydrogen or C$_{1-5}$-alkyl; or a pharmaceutically acceptable salt thereof.

2. The compound according to claim 1, wherein n is 0.

3. A pharmaceutical composition for use in treating a central nervous system ailment associated with the NMDA receptor-associated glycine site comprising an effective amount of a compound according to claim 1 together with a pharmaceutically acceptable carrier or diluent.

4. The pharmaceutical composition according to claim 3 in the form of an oral dosage unit containing about 1–200 mg of the active compound.

5. A method of treating a central nervous system ailment associated with the NMDA receptor-associated glycine site in a person in need thereof comprising administering an effective amount of a compound according to claim 1.

6. A method of treating a central nervous system ailment associated with the NMDA receptor-associated glycine site in a subject in need thereof comprising administering a pharmaceutical composition according to claim 3.

* * * * *